United States Patent
Liu et al.

[11] Patent Number: 6,126,698
[45] Date of Patent: Oct. 3, 2000

[54] CONTINUOUS BIOPOLISHING OF CELLULOSE-CONTAINING FABRICS

[75] Inventors: Jiyin Liu, Raleigh; Brian Condon, Wake Forest, both of N.C.

[73] Assignee: Novo Nordisk Biochem North America, Inc., Franklinton, N.C.

[21] Appl. No.: 09/215,042

[22] Filed: Dec. 17, 1998

Related U.S. Application Data

[60] Provisional application No. 60/068,274, Dec. 19, 1997, abandoned.

[51] Int. Cl.[7] .............................. D06M 16/00; D06P 3/58
[52] U.S. Cl. ................................ 8/401; 8/116.1; 435/263
[58] Field of Search ...................... 8/401, 116.1; 435/263

[56] References Cited

U.S. PATENT DOCUMENTS

| | | | |
|---|---|---|---|
| 5,466,601 | 11/1995 | Jenkins et al. | 8/401 |
| 5,707,858 | 1/1998 | Screws et al. | 8/401 |
| 5,866,407 | 2/1999 | Foody et al. | 8/401 |
| 5,904,736 | 5/1999 | Maurer et al. | 8/401 |
| 5,912,407 | 6/1999 | Miller et al. | 8/139 |

FOREIGN PATENT DOCUMENTS

| | | |
|---|---|---|
| WO 93/20278 | 10/1993 | WIPO . |
| WO 96/02551 | 2/1996 | WIPO . |
| WO 96/17994 | 6/1996 | WIPO . |
| WO 98/33895 | 8/1998 | WIPO . |

*Primary Examiner*—Caroline D. Liott
*Attorney, Agent, or Firm*—Steve T. Zelson, Esquire; Reza Green, Esquire

[57] ABSTRACT

A method for continuously biopolishing cellulose-containing fabrics is disclosed. This method involves (a) contacting the fabric with a cellulase having low affinity for cellulose and (b) subjecting the contacted fabric to high temperature. Treatment of the cellulose-containing material may be carried out as an additional step or a combined step with chemical preparation, dyeing, printing and finishing. This treatment results in excellent pilling performance, minimal loss in fabric strength and weight, and better wettability.

14 Claims, 2 Drawing Sheets

FIG 1

FIG 2

SEQUENCE LISTING

```
<160> NUMBER OF SEQ ID NOS: 2

<210> SEQ ID NO 1
<211> LENGTH: 319
<212> TYPE: PRT
<213> ORGANISM: Escherichia coli

<400> SEQUENCE: 1

Met Ser Lys Lys Lys Phe Val Ile Val Ser Ile Leu Thr Ile Leu Leu
 1               5                  10                  15

Val Gln Ala Ile Tyr Phe Val Glu Lys Tyr His Thr Ser Glu Asp Lys
             20                  25                  30

Ser Thr Ser Asn Thr Ser Ser Thr Pro Pro Gln Thr Thr Leu Ser Thr
         35                  40                  45

Thr Lys Val Leu Lys Ile Arg Tyr Pro Asp Asp Gly Glu Trp Pro Gly
     50                  55                  60

Ala Pro Ile Asp Lys Asp Gly Asp Gly Asn Pro Glu Phe Tyr Ile Glu
 65                  70                  75                  80

Ile Asn Leu Trp Asn Ile Leu Asn Ala Thr Gly Phe Ala Glu Met Thr
                 85                  90                  95

Tyr Asn Leu Thr Ser Gly Val Leu His Tyr Val Gln Gln Leu Asp Asn
            100                 105                 110

Ile Val Leu Arg Asp Arg Ser Asn Trp Val His Gly Tyr Pro Glu Ile
        115                 120                 125

Phe Tyr Gly Asn Lys Pro Trp Asn Ala Asn Tyr Ala Thr Asp Gly Pro
    130                 135                 140

Ile Pro Leu Pro Ser Lys Val Ser Asn Leu Thr Asp Phe Tyr Leu Thr
145                 150                 155                 160

Ile Ser Tyr Lys Leu Glu Pro Lys Asn Gly Leu Pro Ile Asn Phe Ala
                165                 170                 175
```

-continued

```
Ile Glu Ser Trp Leu Thr Arg Glu Ala Trp Arg Thr Thr Gly Ile Asn
            180                 185                 190

Ser Asp Glu Gln Glu Val Met Ile Trp Ile Tyr Tyr Asp Gly Leu Gln
            195                 200                 205

Pro Ala Gly Ser Lys Val Lys Glu Ile Val Val Pro Ile Ile Val Asn
            210                 215                 220

Gly Thr Pro Val Asn Ala Thr Phe Glu Val Trp Lys Ala Asn Ile Gly
225                 230                 235                 240

Trp Glu Tyr Val Ala Phe Arg Ile Lys Thr Pro Ile Lys Glu Gly Thr
                    245                 250                 255

Val Thr Ile Pro Tyr Gly Ala Phe Ile Ser Val Ala Ala Asn Ile Ser
                260                 265                 270

Ser Leu Pro Asn Tyr Thr Glu Leu Tyr Leu Glu Asp Val Glu Ile Gly
                275                 280                 285

Thr Glu Phe Gly Thr Pro Ser Thr Thr Ser Ala His Leu Glu Trp Trp
                290                 295                 300

Ile Thr Asn Ile Thr Leu Thr Pro Leu Asp Arg Pro Leu Ile Ser
305                 310                 315
```

<210> SEQ ID NO 2
<211> LENGTH: 288
<212> TYPE: PRT
<213> ORGANISM: Dictyoglomus sp.

<400> SEQUENCE: 2

```
Met Lys Lys Ser Leu Leu Ser Leu Ile Leu Ile Leu Leu Leu Ile Thr
1                   5                   10                  15

Leu Ser Phe Ser Gln Thr Pro Lys Tyr Lys Asp Ala Phe Ile Leu Lys
                20                  25                  30

Ala Pro Ser Ser Gly Asp Val Thr Thr Lys Asn Leu Pro Leu Thr Leu
            35                  40                  45

Glu Leu Asn Phe Trp Asn Ile Ala Asn Tyr Glu Gly Asn Thr Trp Met
50                  55                  60

Ala Phe Tyr Lys Glu Glu Asp Thr Val Glu Tyr Tyr Ala Asp Ile Lys
65                  70                  75                  80

Asn Ile Val Leu Lys Asp Lys Asn Ser Trp Val His Gly Tyr Pro Glu
                85                  90                  95

Val Tyr Tyr Gly Tyr Lys Pro Trp Ala Gly His Gly Asn Ser Ile Glu
            100                 105                 110

Lys Leu Ala Leu Pro Lys Lys Val Ser Glu Phe Pro Asp Val Leu Phe
        115                 120                 125

Asn Leu Lys Tyr Asn Ile Trp Tyr Glu Lys Asn Leu Pro Ile Asn Phe
    130                 135                 140

Ala Met Glu Thr Trp Ile Thr Lys Glu Pro Tyr Gln Lys Thr Val Thr
145                 150                 155                 160

Ser Gly Asp Ile Glu Met Met Val Trp Leu Tyr Ala Asn Arg Leu Ser
                165                 170                 175

Pro Ala Gly Arg Lys Val Gly Glu Val Lys Ile Pro Ile Ile Leu Asn
            180                 185                 190

Gly Asn Gln Lys Asp Ile Ile Trp Glu Val Tyr Leu Ser Pro Met Ser
        195                 200                 205

Trp Asp Tyr Val Ala Tyr Lys Ser Lys Glu Asn Ile Leu Gln Gly Gln
    210                 215                 220

Val Lys Ile Pro Ile Asn Glu Phe Leu Lys His Leu Arg Thr Ile Leu
225                 230                 235                 240
```

-continued

```
Ala Asn Asn Pro Ser Arg Ile Thr Pro Glu Lys Phe Asp Gln Met Tyr
            245                 250                 255

Val Thr Val Trp Glu Ile Gly Thr Glu Phe Gly Asp Pro Tyr Thr Thr
            260                 265                 270

Glu Ala Lys Phe Gly Trp Thr Phe Ser Asn Phe Asp Ile Glu Leu Lys
            275                 280                 285
```

CONTINUOUS BIOPOLISHING OF CELLULOSE-CONTAINING FABRICS

This application is a continuation of provisional application Ser. No. 60/068,274, filed Dec. 19, 1997, now abandoned, the contents of which are incorporated herein by reference.

FIELD OF THE INVENTION

The present invention relates to methods for treating cellulose-containing fabrics to achieve better fabric handle, appearance and pilling resistance, particularly using continuous or semi-continuous biopolishing processes.

BACKGROUND OF THE INVENTION

Most newly manufactured cellulose-containing fabrics have a handle that is rather hard and stiff unless they are treated with finishing components. In addition, the fabric surface appears not smooth due to small fuzzy fibers protruding from its surface. Furthermore, after a relatively short period of wear, pilling appears on the fabric surface, giving it an unappealing, worn look. For these reasons, improving fabric handle, appearance and pilling resistance is one of the main goals of the textile industry. However, only partial success has been achieved.

A high degree of fabric softness and smoothness can be obtained by using fine, i.e., low-denier, yarns in weaving. However, the resulting cost is high as the loom output decreases proportionately with the weft yarn diameter.

A less expensive way of ensuring a soft and smooth fabric handle is to impregnate the finished fabric with a softening agent, typically a cationic, sometimes silicone-based, surface active compound. However, this treatment does not remove pills and fuzz. Furthermore, the fabric obtains a somewhat greasy handle and is not wash-proof and its moisture absorbency is often considerably reduced.

One chemical method is crosslinking fibers to reduce the fibrillation (Nicolai et al, 1996, *Textile Res. J.* 66(9) 575–580). However, this method causes a decrease in fiber tenacity.

Another known method for obtaining a soft and smooth fabric is treating cellulosic fabrics with cellulases. See, Bazin et al., "Enzymatic Bio-Polishing of Cellulosic Fabric," presented at the 58th Congress of the Association of Chemists and the Textile Industry in Mulhouse, France (Oct. 25, 1991) and Asferg et al., "Softening and polishing of cotton fabrics by cellulase treatment," ITB Dyeing/Printing/Finishing (February 1990). Cellulase treatment of the fabric surface improves fabric quality with respect to handle, appearance and pilling resistance. The most important effects are less fuzz and pilling, increased gloss/luster, improved fabric handle, increased durable softness, and improved water absorbency. These effects are referred to as biopolishing effects. The particular conditions that are utilized are important in determining the outcome of the treatment.

Many processes require exposing the fabric to mechanical agitation to obtain satisfactory biopolishing results. See, for example, WO 9320278; Cavaco-Paulo et al. (1994, *Biocatalysis* 10:353–360); and Cavaco-Paulo et al. (1996, *Textile Res. J.* 66:287–294). However, under some conditions, significant weight loss and strength loss are also observed.

Current methods in cellulase biopolishing are mainly batch processes. The common continuous or semi-continuous processes such as pad-steamer/J-box are not used because they do not provide high mechanical action and use only small volumes of solution and thus result in insufficient and/or uneven biopolishing. For example, non-uniform biopolishing can result from the use of a cellulase complex, in part because different cellulases exhibit different affinities for cellulose and thus are differentially bound by the fabric.

Thus, there is a need in the art for effective biopolishing methods that can be used in conventional continuous or semi-continuous processes.

SUMMARY OF THE INVENTION

The present invention provides a method for treating a cellulose-containing fabric to improve at least one polished property of the fabric. The method is carried out by the steps of (a) contacting the fabric with an aqueous bulk solution comprising a cellulase, wherein the cellulase has a low affinity for cellulose, and (b) subjecting the contacted fabric to high temperature.

Preferably, the method is carried out in a continuous or semi-continuous apparatus. In these embodiments, the method further comprises, after step (a), removing the contacted fabric from the bulk solution. In preferred embodiments, the fabric is contacted with the bulk solution for less than about 5 minutes, most preferably, for less than about 1 minute. The contacting and subjecting steps may be performed sequentially or simultaneously.

The polished property may be one or more of pilling note, handle, and appearance. In preferred embodiments, the methods of the invention result in an improvement in pilling note of at least about 0.25; more preferably, at least about 0.5; and most preferably, at least about 1.0.

The low-affinity cellulases are preferably enzymes that exhibit thermostable cellulase activity. Typically, the bulk solution contains less than about 200 CMCU/ml of cellulase activity, preferably less than about 100 CMCU/ml, and more preferably, less than about 50 CMCU/ml.

In other aspects, the invention provides methods for combined biopolishing and dyeing, or combined biopolishing and scouring. In these embodiments, the aqueous solution with which the fabric is contacted contains, in addition to the low-affinity cellulase, other appropriate components such as, e.g., dyes and auxiliary compounds.

DETAILED DESCRIPTION OF THE INVENTION

The present invention provides biopolishing methods that enhance the quality of cellulosic fabrics. The methods are carried out by (i) contacting a cellulosic fabric, preferably in a continuous or semi-continuous apparatus, with an aqueous bulk solution comprising at least one cellulase that exhibits a low affinity for cellulose and (ii) subjecting the cellulase-contacted fabric to a high temperature.

Biopolishing as used herein refers to a treatment that is directed towards improving one or more of the following properties: fabric handle, appearance, and pilling resistance. The methods allow uniform action by the cellulase(s) on the fabric and result in measurable improvements in one or more of these properties, while minimizing loss of fabric weight and/or fabric strength and obviating the need for mechanical agitation. The present invention minimizes loss of cellulase from the aqueous solution via adsorption to the fabric, and thereby allows the use of conventional semi-continuous or continuous textile industry equipment. The methods of the invention can also be combined with processes such as alkaline chemical preparation, fabric dyeing, printing, and finishing, thereby affording increased flexibility in textile manufacturing. Furthermore, the simultaneous use of other enzymes, such as, e.g., lipase, protease, hemicellulases, and/or pectinases, allows the simultaneous removal of cellulosic and non-cellulosic materials. Finally, the methods of the invention can reduce the formation of lint dust during subsequent sewing and home laundry of fabrics treated according to the invention.

Cellulosic fabrics as used herein encompass both knitted and woven structures made from cellulosic fibers, including, without limitation, cotton, flax, ramie, hemp, jute, rayon/viscose, tencel/lyocell, or their blends, as well as fabrics made blends of cellulosic fibers and other natural and/or manmade fibers such as, e.g., wool, silk, polyester, nylon, and the like.

A continuous or semi-continuous apparatus as used herein refers, without limitation, to conventional equipment such as, e.g., pad-steamer-washing boxes or pad-J boxes, in which the fabric is wetted by contact with a bulk solution, and, once passed through, is no longer in direct contact with the bulk solution. This is distinguished from equipment in which the fabric is in continuous contact with a bulk solution throughout the treatment (batch methods). In a batch apparatus, the liquid:fabric ratio (weight of solution used per weight of fabric) is generally greater than about 400%, as compared with a wet pick-up (weight of solution absorbed per weight of fabric) of between about 50% and about 150% in a continuous or semi-continuous apparatus. It will be understood that the present invention encompasses the use of any configuration or apparatus in which the fabric is only exposed to the bulk solution for a short time relative to the total treatment time, with or without padding to remove excess solution from the fabric.

"High temperature" as used herein refers to temperatures above about 65° C., preferably above about 70° C., and most preferably above about 90° C.

Cellulases

In practicing the present invention, a cellulosic fabric is contacted with a cellulase that exhibits a low affinity for cellulose. As used herein, a cellulase or cellulolytic enzyme is an enzyme that hydrolyzes cellulose, including, without limitation, 1,4-β-D-glucan cellobiohydrolase (EC 3.2.1.91), endo-β-1,4-D-glucan-4-glucanohydrolase (EC 3.2.1.4), and β-glucosidase (EC 3.2.1.21). Cellulase enzymatic activity (expressed as endoglucanase units or CMCU) is typically determined by incubating an enzyme with carboxymethylcellulose (CMC) at pH 7.5 for 20 min, after which the formation of reducing sugars is determined using the p-hydroxybenzoic acid-hydrazide (PHBAH) reaction (Lever, 1972, Anal. Biochem. 47:273–279, with the modification that 5 g potassium sodium tartrate is added in addition to 1.5 g of PHBAH).

Enzymes having a low affinity for cellulose, also referred to as "low-affinity cellulases", may be identified using, for example, the method described in Example 4 below, which involves incubation of the enzyme with Avicel to allow binding, followed by elution and detection of bound enzyme. Typically, an enzyme having a low affinity for cellulose will not exhibit binding to Avicel in this assay. The use of enzymes having higher affinity for cellulose is disadvantageous in a continuous or semi-continuous apparatus, because it results in (a) non-uniform adsorption of enzyme to the fabric and (b) loss of enzyme from the bulk solution because of adsorption to the fabric.

A cellulase having low affinity for cellulose generally lacks a functional cellulose-binding domain (CBD), either intrinsically or subsequent to modification of the cellulase sequence. CBDs are peptide sequences that confer high-affinity binding to cellulose, including, without limitation, sequences defined by Peter Tomme et al. in "Cellulose-Binding Domains: Classification and Properties" in *Enzymatic Degradation of Insoluble Carbohydrates*, John N. Saddler and Michael H. Penner (Eds.), ACS Symposium Series, No. 618, 1996. Tomme et al. classified more than 120 cellulose-binding domains into ten families (designated I–X), and identified CBDs in various enzymes such as cellulases, xylanases, mannanases, arabinofuranosidases, acetyl esterases and chitinases, as well as in non-hydrolytic polysaccharide-binding proteins. Low-affinity cellulases according to the present invention may either lack a CBD sequence entirely, or may contain a residual CBD sequence that has been modified to destroy its cellulose-binding activity, by deletion, addition, and/or substitution of one or more residues or by any chemical or enzymatic modification of the intact protein; such a modified sequence is also referred to as a non-functional CBD.

According to the invention, a fabric that has been contacted with a low-affinity cellulase is also exposed to high temperatures. Accordingly, the cellulases used in practicing the invention are preferably thermostable, i.e., exhibit optimal cellulase enzymatic activity at a temperature of at least about 55° C., preferably at least about 65° C., more preferably at least about 75° C. and most preferably at least about 85° C. Any low-affinity cellulase may be used in practicing the invention, so long as it exhibits at least about 20% of its maximal enzymatic activity at a temperatures above about 65° C. Preferably, the cellulase exhibits at least about 50% of its maximal activity at a temperature of about 65° C.

Non-limiting examples of cellulases useful in practicing the present invention include the cellulase from Pyrococcus whose sequence is depicted in SEQ ID NO:1 and the cellulase from Dictyoglomus whose sequence is depicted in SEQ ID NO:2. Other suitable cellulases include, without limitation, cellulases derived from the following thermophilic cellulases, which have been modified if necessary to reduce their affinity for cellulose: β-glucosidase from *Pyrococcus furiosus* (Kengen et al., 1993, *Eur.J.Biochem.* 213:305); exoglucanase from Thermotoga sp. (Ruttersmith et al., 1991, *Biochem.J.* 277:887); cellulases from *Thermotoga maritima* (Bronnenmeier et al, 1995, *Appl. Environ. Microbiol.* 61:1399; *Microbiology* 142:2532, 1996); β-glucosidase from *Thermotoga maritima* (Gabelsberger et al., 1993, *FEMS Microbiol. Lett.* 109:131); endoglucanase B from *Thermotoga neapolitania* (Bok et al., 1994, *ACS Symp. Ser.* 566:54); endoglucanase from Archebacteria (WO 97/44361); endoglucanase from *Acidothermus cellulolyticus* (WO 96/02551); cellulase from *Rhodothermus marinus* (Hreggvidsson et al., 1996, *Environ. Microbiol.* 62:3047); and an exocellulase/endocellulase from *Caldocellum saccharolyticum* (Saul, *Nuc.Acids Res.* 17:439, 1989).

The cellulases may be obtained from their cell of origin or from a recombinant organism that has been programmed to synthesize the cellulase from a heterologous gene. Preferably, the cellulases are monocomponent enzymes, i.e., are single polypeptides having a defined enzymatic activity that are not synthesized as part of a multicomponent complex exhibiting multiple enzymatic activities. The cellulases may be recovered by conventional procedures including, but not limited to, centrifugation, filtration, spray-drying, evaporation, or precipitation. As used herein, "purified" or "isolated" cellulase is cellulase that has been treated to remove non-cellulase material derived from the cell in which it was synthesized that could interfere with its enzymatic activity. If the cellulase is secreted into the culture medium, purification may comprise separating the culture medium from the biomass by centrifugation, filtration, or precipitation, using conventional methods. Alternatively, the cellulase may be released from the host cell by cell disruption and separation of the biomass. In some cases, further purification may be achieved by conventional protein purification methods, including without limitation ammonium sulfate precipitation; acid or chaotrope extraction; ion-exchange, molecular sieve, and hydrophobic chromatography, including FPLC and HPLC; preparative isoelectric focusing; and preparative polyacrylamide gel electrophoresis. Alternatively, purification may be achieved using affinity chromatography, including immunoaffinity chromatography. For example, hybrid recombinant cellulases may be used having an additional amino acid sequence that serves as an affinity "tag", which facilitates purification using an appropriate solid-phase matrix.

Other Components

In some embodiments of the invention, the bulk solution containing the low-affinity cellulase further comprises other components, including without limitation other enzymes, as well as one or more of surfactants, bleaching agents, anti-foaming agents, builder systems, and the like, that enhance the biopolishing process and/or provide superior effects related to, e.g., dyeability and/or wettability. The aqueous solution may also contain dyeing agents.

Enzymes suitable for use in the present invention include without limitation:

Pectin-digesting enzymes: Suitable pectin-digesting enzymes (some of which are identified by their Enzyme Classification numbers in accordance with the Recommendations (1992) of the International Union of Biochemistry and Molecular Biology (IUBMB)) include, without limitation, pectin-degrading enzymes such as pectate lyase, pectin lyase, pectin methyl esterase, polygalacturonase (3.2.1.15), and rhamnogalacturonase (WO 92/19728).

Hemicellulases: Suitable hemicellulases include without limitation endo-arabinanase (3.2.1.99, Rombouts et al., Carb. Polymers 9:25, 1988), arabinofuranosidase, endo-β-1,4-galactanase, endo-xylanase (3.2.1.8), mannanase, and xyloglucanase.

Amylases: Suitable amylases include α-amylases (α-1,4 glucan-4-glucanohydrolase, EC 3.2.1.1), including, without limitation, Bacillus α-amylases (which in the present context are termed "Termamyl-like α-amylases"), including B. licheniformis, B. amyloliquefaciens, and B. stearothermophilus α-amylase. Commercially available Termamyl-like B. licheniformis α-amylases are Optitherm® and Takatherm® (available from Solvay), Maxamyl® (available from Gist-brocades/Genencor), Spezym AA® (available from Genencor), and Keistase® (available from Daiwa). Non-Termamyl-like α-amylase include, without limitation, members of the Fungamyl-like α-amylase family.

Proteases: Suitable proteases include those of animal, vegetable or microbial origin, preferably of microbial origin. The protease may be a serine protease or a metalloprotease, preferably an alkaline microbial protease or a trypsin-like protease. Examples of proteases include aminopeptidases, including prolyl aminopeptidase (3.4.11.5), X-pro aminopeptidase (3.4.11.9), bacterial leucyl aminopeptidase (3.4.11.10), thermophilic aminopeptidase (3.4.11.12), lysyl aminopeptidase (3.4.11.15), tryptophanyl aminopeptidase (3.4.11.17), and methionyl aminopeptidase (3.4.11.18); serine endopeptidases, including chymotrypsin (3.4.21.1), trypsin (3.4.21.4), cucumisin (3.4.21.25), brachyurin (3.4.21.32), cerevisin (3.4.21.48) and subtilisin (3.4.21.62); cysteine endopeptidases, including papain (3.4.22.2), ficain (3.4.22.3), chymopapain (3.4.22.6), asclepain (3.4.22.7), actinidain (3.4.22.14), caricain (3.4.22.30) and ananain (3.4.22.31); aspartic endopeptidases, including pepsin A (3.4.23.1), Aspergillopepsin I (3.4.23.18), Penicillopepsin (3.4.23.20) and Saccharopepsin (3.4.23.25); and metalloendopeptidases, including Bacillolysin (3.4.24.28).

Non-limiting examples of subtilisins include subtilisin BPN', subtilisin amylosacchariticus, subtilisin 168, subtilisin mesentericopeptidase, subtilisin Carlsberg, subtilisin DY, subtilisin 309, subtilisin 147, thermitase, aqualysin, Bacillus PB92 protease, proteinase K, protease TW7, and protease TW3.

Commercially available proteases include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Also contemplated for use in the present invention are protease variants, such as those disclosed in EP 130.756 (Genentech), EP 214.435 (Henkel), WO 87/04461 (Amgen), WO 87/05050 (Genex), EP 251.446 (Genencor), EP 260.105 (Genencor), Thomas et al., (1985), Nature 318:375–376, Thomas et al., (1987), J. Mol. Biol., 193, pp. 803–813, Russel et al., (1987), Nature 328:496–500, WO 88/08028 (Genex), WO 88/08033 (Amgen), WO 89/06279 (Nove Nordisk A/S), WO 91/00345 (Nove Nordisk A/S), EP 525 610 (Solvay) and WO 94/02618 (Gist-Brocades N.V.).

The activity of proteases can be determined as described in "Methods of Enzymatic Analysis", third edition, 1984, Verlag Chemie, Weinheim, vol. 5.

Lipases. Suitable lipases (also termed carboxylic ester hydrolases) include those of bacterial or fungal origin, including triacylglycerol lipases (3.1.1.3) and Phospholipase $A_2$ (3.1.1.4.). Lipases for use in the present invention include, without limitation, lipases from Humicola (synonym Thermomyces), such as from H. lanuginosa (T. lanuginosus) as described in EP 258 068 and EP 305 216 or from H. insolens as described in WO 96/13580; a Pseudomonas lipase, such as from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012); a Bacillus lipase, such as from B. subtilis (Dartois et al., Biochem.Biophys. Acta, 1131:253–360, 1993), B. stearothermophilus (JP 64/744992) or B. pumilus (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™, Lipozyme™, Palatase™, Novozym™435, and Lecitase™ (all available from Novo Nordisk A/S). The activity of the lipase can be determined as described in "Methods of Enzymatic Analysis", Third Edition, 1984, Verlag Chemie, Weinhein, vol. 4.

Preferably, the enzymes are derived from alkalophilic microorganisms and/or exhibit enzymatic activity at elevated temperatures. The enzymes may be isolated from their cell of origin or may be recombinantly produced, and may be chemically or genetically modified. Typically, the enzymes are incorporated in the aqueous solution at a level of from about 0.0001% to about 1% of enzyme protein by weight of the composition, more preferably from about 0.001% to about 0.5% and most preferably from 0.01% to 0.2%. It will be understood that the amount of enzymatic activity units for each additional enzyme to used in the methods of the present invention in conjunction with a particular cellulase can be easily determined using conventional assays.

Surfactants suitable for use in practicing the present invention include, without limitation, nonionic (U.S. Pat. No. 4,565,647); anionic; cationic; and zwitterionic surfactants (U.S. Pat. No. 3,929,678); which are typically present at a concentration of between about 0.002% to about 3% by weight, preferably from about 0.02% to about 2% by weight. Anionic surfactants include, without limitation, linear alkylben-zenesulfonate, α-olefinsulfonate, alkyl sulfate (fatty alcohol sulfate), alcohol ethoxysulfate, secondary alkanesulfonate, alpha-sulfo fatty acid methyl ester, alky- or alkenylsuccinic acid, and soap. Non-ionic surfactants include, without limitation, alcohol ethoxylate, nonylphenol ethoxylate, alkylpolyglycoside, alkyldimethylamine-oxide, ethoxylated fatty acid monoethanolamide, fatty acid monoethanolamide, polyhydroxy alkyl fatty acid amide, and N-acyl N-alkyl derivatives of glucosamine ("glucamides").

Builder systems include, without limitation, aluminosilicates, silicates, polycarboxylates and fatty acids, chelating agents such as ethylenediamine tetraacetate, aminopolyphosphonates, particularly ethylenediamine tetramethylene phosphonic acid, and diethylene triamine pentamethylenephosphonic acid, which are included at a concentration of between about 5% to 80% by weight, preferably between about 5% and about 30% by weight.

Bleaching systems may comprise an oxidizing agent such as hydrogen peroxide, perborate, peracetate, or percarbonate, which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

Antifoam agents include without limitation silicones (U.S. Pat. No. 3,933,672; DC-544 (Dow Corning), which are typically included at a concentration of between about 0.01% and about 1% by weight.

The compositions may also contain soil-suspending agents, soil-releasing agents, optical brighteners, abrasives, and/or bactericides, as are conventionally known in the art.

Dyeing agents including, without limitation, dyes disclosed in Shore (ed.), *Cellulosic Dyeing*, 1995 (Society of Dyers and Colorists, Alden Press, Oxford).

Biopolishing Methods

The present invention provides methods for biopolishing fabric which comprise (a) contacting a cellulosic fabric, preferably in a continuous or semi-continuous apparatus, with an aqueous solution comprising at least a low-affinity cellulase and (b) subjecting the contacted fabric to a high temperature. The contacting step involves exposing the fabric relatively briefly (typically, for less than 5 min) to a bulk solution containing the enzyme, after which the fabric may be padded to remove excess solution. This results in a wet pick-up (expressed as weight of solution:weight of fabric×100) of between about 50 and about 200%, preferably between about 50 and about 130%. The contacting and subjecting steps may be performed simultaneously (i.e., by contacting the fabric with the bulk solution while heating) or sequentially (i.e., by first contacting the fabric with the bulk solution; optionally removing excess solution; and, subsequently, subjecting the wetted fabric to high temperature).

To achieve effective biopolishing, the concentration of enzyme in the aqueous solution (CMCU/ml), the temperature to which the fabric is subjected, and the total incubation time, will vary, depending on:

(i) the nature of the fabric;
(ii) the particular low-affinity cellulase used;
(iii) the pH of the solution;
(iv) the time during which the fabric is contacted with the bulk solution; and
(v) the presence of other components in the aqueous solution.

Determination of suitable enzyme concentration to be used, as well as optimization of other variables, can be achieved using only routine experimentation by establishing a matrix of conditions and testing different points in the matrix. For example, the enzyme concentration, the temperature at which the contacting occurs, and the time of contact can be varied, after which the resulting fiber or textile is evaluated for (a) one or more biopolished properties, such as, e.g., fabric handle, appearance, or pilling resistance, and, optionally, (b) potential loss in fabric strength and/or weight.

Fabric handle and appearance are evaluated by panel testing, using a rating of 1–3 (worst to best).

Pilling can be measured using any conventional method, such as, e.g., according to American Society for Testing and Materials protocol ASTM D 4970-89, using a Martindale Abrasion and Pilling Tester (James H. Heal & Co, UK). In this method, pilling is evaluated visually on a scale of 1 to 5, where 1 signifies severe pilling and 5 signifies no pilling.

Fabric strength is measured using any conventional method, such as, e.g., according to ASTM protocol D 3786-87, using a Mullen Burst tester (Model C, B. F. Perkins, Chicopee Mass.).

In practicing the invention, conditions are selected in which one or more biopolished properties, particularly pilling, show improvements over untreated controls, but in which fabric strength loss is minimal. Preferably, a pilling note increase of at least about 0.25 is observed, more preferably at least about 0.5, and most preferably at least about 1.0. Preferably, fabric strength loss is less than about 20%, more preferably less than about 10%, and most preferably less than about 5%.

Typically, the bulk solution contains a low-affinity cellulase at a concentration of less than about 200 CMCU/ml, more preferably less than about 100 CMCU/ml, and most preferably less than about 50 CMCU/ml; at a temperature of at least about 65° C., preferably at least about 75° C., and most preferably at least about 85° C.; and at a pH of between about 4 and 12, preferably between about 5 and 10, and most preferably between about 7 and 10.

Combination methods: The present invention also encompasses combination methods in which biopolishing is carried out simultaneously with scouring and/or dyeing. In these embodiments, the aqueous bulk solution also contains other components, including without limitation the enzymes disclosed herein, as well as other components, such as, e.g., dyes (including without limitation reactive dyes, direct dyes, sulphur dyes, and vat dyes) and dye auxiliaries. See, Shore (ed.), *Cellulosic Dyeing*, 1995 (Society of Dyers and Colorists, Alden Press, Oxford). The contacted fabric is then subjected to a high temperature, which results in simultaneous dyeing or scouring and biopolishing.

The following examples are intended as non-limiting illustrations of the present invention.

EXAMPLE 1

Biopolishing Using Dictyoglomus Cellulase

The following experiment was performed to evaluate the biopolishing capability of Dictyoglomus cellulase in a continuous apparatus.

Methods:

The fabric used was Knitted Fabric 460 (Test Fabrics Inc.), which is 100% cotton bleached interlock. The fabric was cut into 20×30 cm pieces weighing about 12.5 g each. The weight of each swatch was determined after conditioning for at least 24 hours at 65±2% relative humidity and 21±2° C. (70±3° F.).

The cellulase comprised the catalytic domain from Dictyoglomus cellulase (whose sequence is shown in SEQ ID NO:2) which was formulated in 15 mM sodium phosphate. The pH and enzyme concentration were as shown in Table 1 below.

Swatches were contacted with enzyme solutions for less than 45 seconds and then padded through a pad, after which they were weighed and hung immediately in a Mathis steam range (Type PSA-HTF) (Werner Mathis USA Inc. Concord, N.C.). The percentage of solution on fabric (% wet pick-up) and ratio of cellulase activity to fabric are shown in Table 1. Fabric swatches were treated at 90° C. and 100% relative humidity for 90 minutes. All swatches were then transferred and rinsed in de-ionized water for at least 5 minutes, after which they were air dried. Finally, the swatches were conditioned at 65±2% relative humidity and 21±2° C. (70±3° F.) temperature for at least 24 hours before evaluation.

Fabric strength was measured on Mullen Burst tester model C according to ASTM D3786-87: Standard Test Method for Hydraulic Bursting Strength of Knitted Goods and Nonwoven Fabrics-Diaphragm Bursting Strength Tester Method. The results are presented as the average of at least 8 measurements. Pilling note was measured according to ASTM D 4970-89: Standard Test Method for Pilling Resistance and Other Related Surface Changes of Textiles Fabrics (Martindale Pressure Tester Method). After 500 revolutions, pilling on the fabric was evaluated visually against a standard scale 1 to 5, where 1 indicates very severe pilling and 5 indicates no pilling. The results are presented as the average of at least two measurements.

Figure 1:
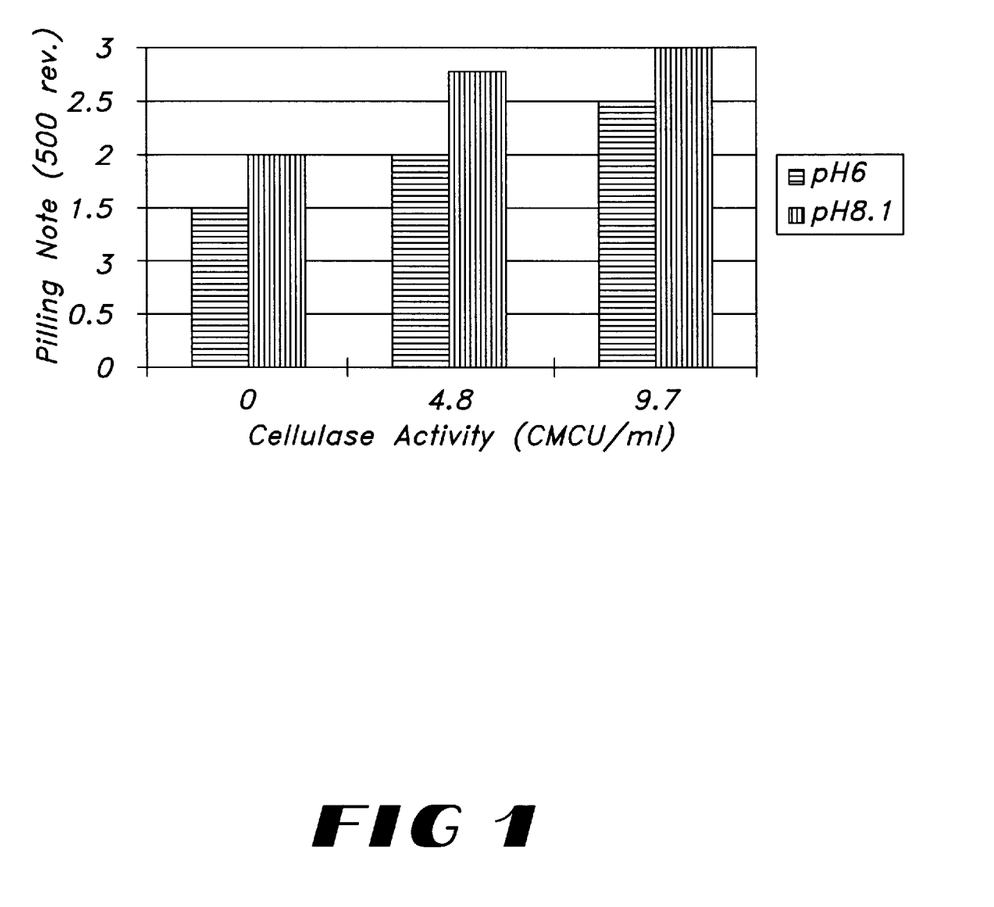

Results:

The results are shown in Table 1 below and in FIG. 1. As the concentration of enzyme increased, a corresponding increase in pilling note was observed. The increase in pilling resistance is greater at pH 8.1 than at pH 6.0. Under the indicated conditions of enzyme concentration and pH, the method of the invention results in minimal fabric strength loss (less than 5% loss at pH 6.0 and no detectable loss at pH 8.1). An even pilling on the surface also indicated that the fabric had been exposed uniformly to the cellulase.

These results demonstrate that biopolishing of cotton fabric with Digtyoglomus cellulase improves fabric pilling resistance significantly without detectable strength loss.

Figure 2:
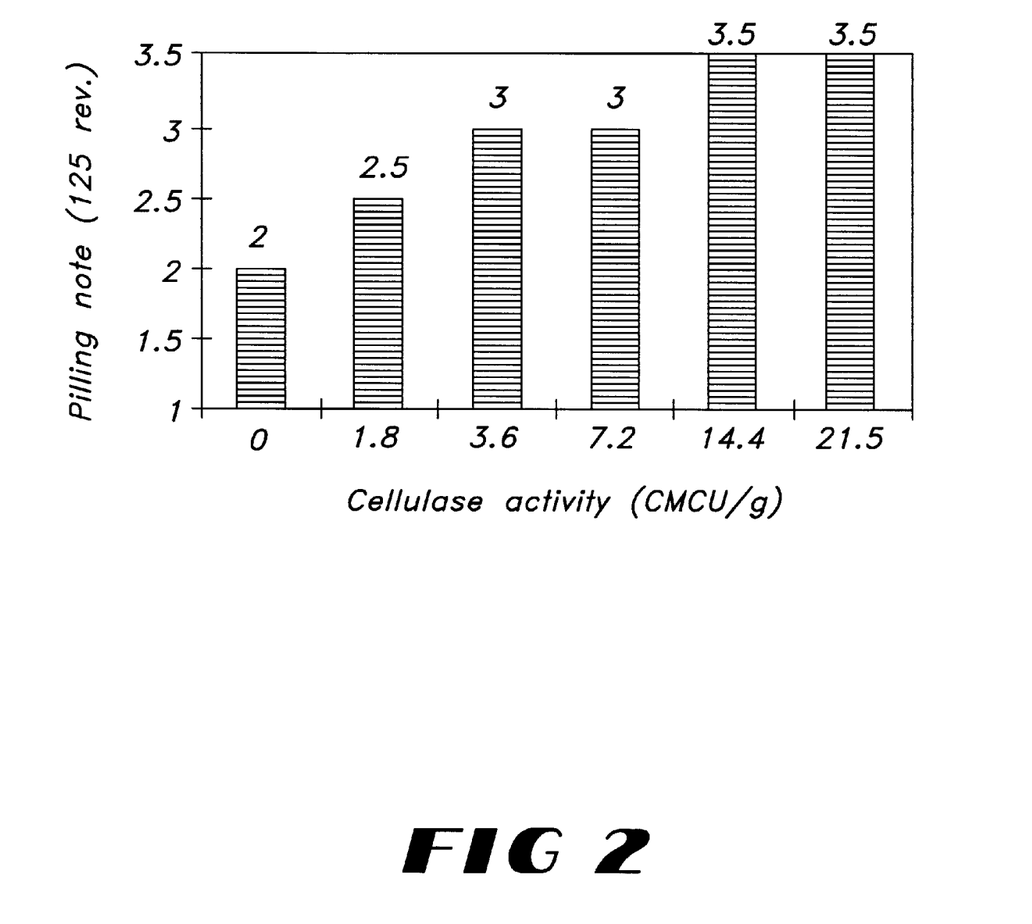

Results:

No statistically significant strength loss was detected for all cellulase-treated swatches when compared with controls that were not exposed to enzymes. On the other hand, pilling note increases as enzyme activity increases (FIG. 2). These results indicated that Pyroccocus cellulases are useful for biopolishing, while causing little fabric strength loss in a Pad Steamer apparatus. A better appearance and fabric handle were also achieved.

EXAMPLE 3

Combination Treatments

The following experiments were performed to evaluate the methods of the present invention in combined scouring and biopolishing.

Methods.

The fabric used was Fabric 4600, which is an unscoured and unbleached 100% cotton fabric. Fabric preparation and buffer were the same as described in Example 2 above.

The bulk solution contained: (a) The Pyroccucus cellulase described in Example 2 above, at a concentration of 6.12 CMCU/ml and 4.9 CMCU/g fabric; and (b) thermostable pectate lyase at a concentration of 1.93 mv-mol/ml/min. Swatches were padded and treated as described in Example 1. The fabric wet pick-up was 80%. Treatment conditions were pH 9.2, 90° C., relative humidity (RH) 100%, and treatment was for 90 min.

The rinsing, drying, evaluating procedures are the same as described in Example 1 above. Wetting speed was evaluated according to the AATCC test method. A water drop from 1 cm high burette was allowed to fall to a taut surface of fabric specimen. The time for water disappearance on the fabric surface was recorded as wetting time. Eight measurements on each specimen were carried out and averaged.

Results:

TABLE 1

| # | SOLUTION PH | CELLULASE SOLUTION (CMCU/ML) | WET PICK-UP (% W/W) | CELLULASE ACTIVITY (CMCU/G FABRIC) | STRENGTH LOSS (%) | PILLING NOTE (500 REV) |
| --- | --- | --- | --- | --- | --- | --- |
| 1 | 6 | 0 | 125 | 0 | 0 | 1.5 |
| 3 | 6 | 4.8 | 130 | 6.2 | 2.4 | 2 |
| 5 | 6 | 9.7 | 137 | 13.3 | 3.5 | 2.5 |
| 2 | 8.1 | 0 | 128 | 0 | 0 | 2 |
| 4 | 8.1 | 4.8 | 131 | 6.3 | 0 | 2.75 |
| 6 | 8.1 | 9.7 | 137 | 13.3 | 0 | 3 |

EXAMPLE 2

Biopolishing Using Pyrococcus Cellulase

The following experiment was performed to evaluate the biopolishing capability of Dictyoglomus cellulase in a continuous apparatus.

Biopolishing was carried out essentially as described in Example 1, except that the buffer used consisted of 9.53 g sodium tetraborate decahydrate dissolved in 2.5 l deionized water and adjusted to pH 9.2, and the cellulase was derived from Pyrococcus (whose sequence is depicted in SEQ ID NO:1).

Methods:

Swatches were padded and treated as described in Example 1. The fabric wet pick-up was 94%. The fabric was treated for 90 min at pH 9.2, 90° C., and relative humidity 100%. The rinsing, drying, evaluating procedures were the same as in Example 1 except that pilling note was evaluated after 125 revolutions.

Fabric pilling resistance improved after either cellulase treatment or combined treatment with cellulase and pectinase (Table 2). Furthermore, the average wetting time also decreased significantly relative to non-enzyme-treated controls (Table 3). These results indicated that the methods of the invention can be used in combined biopolishing and scouring.

TABLE 2

| Pilling Note (125 rev.) | |
| --- | --- |
| non-enzyme | 2 |
| Cellulase | 2.5 |
| Pectinase | 2 |
| Cell + Pect. | 2.5 |

TABLE 3

| | wetting time (second) | | | | | | | | | |
|---|---|---|---|---|---|---|---|---|---|---|
| | 1 | 2 | 3 | 4 | 5 | 6 | 7 | 8 | 9 | Average |
| non-enzyme | 7 | 50 | 115 | 249 | >300 | >300 | >300 | >300 | >300 | >300 |
| Cellulase | 64 | 40 | 40 | 46 | 164 | 124 | 214 | 182 | | 109 |
| Pectinase | 61 | 70 | 65 | 64 | 94 | 96 | 95 | 64 | 104 | 79 |
| Cell + Pect. | 37 | 40 | 39 | 30 | 28 | 22 | 28 | 28 | | 32 |

EXAMPLE 4

Identification of Low-Affinity Cellulases

The following method is used to measure the affinity of a polypeptide for cellulose, in order to identify low-affinity cellulases.

200 μl of a 1 mg/ml enzyme solution is mixed with 200 μl of a 10% (w/v) Avicel suspension, which is made up in 0.1M sodium phosphate buffer, pH 7.5, and mixed for 15 min. The mixture is incubated for 1 h at 4° C., after which it is subjected to centrifugation for 5 min at 5000 rpm in a microfuge. The supernatant is removed, and the Avicel is washed with 1 ml of buffer and re-pelleted. Finally, the Avicel pellet is resuspended in SDS-PAGE loading buffer and incubated at 95° C. for 2 min. After centrifugation for 5 min at 5000 rpm, the supernatant is recovered and loaded on a 4–20% gradient acrylamide SDS gel (Novex), and electrophoresis is performed in an X-cell mini-cell (Novex). Electrophoresis and staining are performed according to the manufacturer's instructions.

Using this method, low-affinity cellulases are identified as cellulases that do not result in a detectable band in SDS-PAGE using Coomassie Blue staining.

All patents, patent applications, and literature references referred to herein are hereby incorporated by reference in their entirety.

Many variations of the present invention will suggest themselves to those skilled in the art in light of the above detailed description. Such obvious variations are within the full intended scope of the appended claims.

What is claimed is:

1. A method for treating a cellulose-containing fabric, said method comprising
    (a) contacting the fabric with an aqueous bulk solution comprising a cellulase, wherein said cellulase lacks a functional cellulose-binding domain, and
    (b) subjecting the contacted fabric to a temperature above about 70° C., wherein said contacting and subjecting steps occur sequentially or simultaneously and wherein said treated fabric exhibits at least one improved polished property relative to an untreated fabric.

2. A method as defined in claim 1, further comprising, after step (a), removing said contacted fabric from said bulk solution.

3. A method as defined in claim 1, wherein the cellulose-containing fabric comprises a cellulosic fiber selected from the group consisting of cotton, flax, ramie, hemp, jute, rayon, lyocell, combinations of any of the foregoing with each other and combinations of any of the foregoing with a non-cellulosic fiber.

4. A method as defined in claim 1, wherein the cellulase exhibits thermostable cellulase enzymatic activity.

5. A method as defined in claim 1, wherein the cellulase is derived from Dictyoglomus or Pyrococcus.

6. A method as defined in claim 1, wherein the cellulase is a monocomponent enzyme.

7. A method as defined in claim 1, wherein the bulk solution contains less than about 200 CMCU/ml of cellulase activity.

8. A method as defined in claim 1, wherein the pH of the aqueous solution is between about 4 and about 12.

9. A method as defined in claim 8, wherein the pH of the aqueous solution is between about 5 and about 10.

10. A method as defined in claim 1, wherein the high temperature is above about 90° C.

11. A method as defined in claim 1, wherein said improved property is selected from the group consisting of pilling note, handle, and appearance.

12. A method as defined in claim 1, wherein said bulk solution further comprises an enzyme selected from the group consisting of proteases, lipases, amylases, pectin-digesting enzymes, and hemicellulases.

13. A method as defined in claim 1, wherein said bulk solution further comprises a dye and wherein said method results in dyeing of said fabric.

14. A method as defined in claim 13, wherein said bulk solution further comprises one or more auxiliary compounds selected from the group consisting of surfactants and chelating agents.

* * * * *